United States Patent [19]

Wheeless

[11] Patent Number: 4,687,327
[45] Date of Patent: Aug. 18, 1987

[54] OIL MIST MONITOR

[75] Inventor: Michael R. Wheeless, Lake Jackson, Tex.

[73] Assignee: The Dow Chemical Company, Midland, Mich.

[21] Appl. No.: 705,751

[22] Filed: Feb. 25, 1985

[51] Int. Cl.$^4$ .............................................. G01N 21/59
[52] U.S. Cl. ....................................... 356/70; 356/435
[58] Field of Search ................. 356/70, 435, 436, 437, 356/438, 439, 442; 250/573, 576

[56] References Cited

U.S. PATENT DOCUMENTS

| | | | |
|---|---|---|---|
| 3,268,734 | 8/1966 | Bjorn | 356/70 |
| 3,417,250 | 12/1968 | Kadivnik | 356/70 |
| 3,838,925 | 10/1974 | Marks | 356/435 |
| 3,847,487 | 11/1974 | Boll | 356/438 |
| 4,185,278 | 1/1980 | Lintelmann et al. | 356/438 |
| 4,544,273 | 10/1985 | Berndt | 356/439 |

Primary Examiner—R. A. Rosenberger

[57] ABSTRACT

An instrument for measuring opacity of oil mist for lubrication purposes is set forth. In the preferred and illustrated embodiment, the apparatus is preferably installed in a pipe cross, opposing legs of the cross conduct oil mist past the opposite two legs supporting an opacity measuring system. Utilizing a bridge voltage supply to power an amplifier forming a reference voltage for reference diodes, a first photo cell is provided with a reference light from LED created light directed to the reference. A second LED directs light through the oil mist. The quantity of light is measured by a second photo cell reflecting the light absorbence of the sample, and the output of the two measuring devices is determined in a differential amplifier, driving a meter movement. The direct current signal is at a safe current range for use of the transmitter in a hazardous environment and is inversely proportional to the percent transmission of the signal.

15 Claims, 4 Drawing Figures

OIL MIST MONITOR

BACKGROUND OF THE DISCLOSURE

This apparatus is directed to an opacity transmitter. It is particularly constructed and arranged for installation with an oil mist generator. An oil mist generator is a device which forms a mist of lubricating oil to be supplied to rotating machinery for lubrication purposes. While other applications can be imagined, this apparatus will be described in the context of an oil mist generator. The mist is delivered through a suitable conduit. As a convenience, a pipe having a two inch ID is suggested, and delivers the mist of oil from a suitable source to a rotating machine requiring such lubrication. If lubrication were to fail, catastrophic failure may follow soon thereafter. The oil misting lubrication system is preferably monitored. This enables the formation of an alarm signal indicative of oil mist failure, thereby providing adequate early warning so that the oil misting apparatus can be checked or the rotating machinery shut down until repairs are made.

Since oil mist monitors are frequently used in an explosive environment, it is desirable to comport with industrial standards for explosion proof equipment. The opacity transmitter therefore employs an electrically insulative case having no lens or windows and its circuitry, operated from a remote power supply in a safe location, is designed to limit maximum current draw to a safe level in the event that a short might occur. Further, certain electrical inspection may be accomplished externally with the transmitter housing in its closed and sealed condition. The oil mist monitor is thus intrinsically safe for use even in areas having an explosive atmosphere.

Typically, the oil mist is formed by a device for this purpose and is delivered through a pipe. As an example for the present disclosure, the pipe is assumed to have a two inch ID whereby a continual flow of air borne oil droplets is delivered to rotating machinery. This apparatus is best installed in the pipe delivering the oil mist to the rotating machinery. A location can be obtained by cutting the pipe, removing a portion thereof, and installing the present invention. It lends itself to easy installation because it is preferably constructed with a pipe cross having four legs at right angles. Two of the legs are located to continue the flow and they are therefore connected in the oil mist delivery system. Two tubular legs are provided at right angled position to the flow path. Within these legs is located the measuring apparatus of this disclosure. The apparatus is typically installed with the opposing tubular legs positioned horizontally to avoid creating a trap in either leg which might permit settling of the droplets to obscure operation of the equipment.

With the foregoing in view, this apparatus is briefly summarized as providing a pipe cross utilizing transverse arms to locate light emitting diodes (LEDs) at one end transmitting light across the oil mist flow path to photo cells at opposite end of the cross. The apparatus provides LED responsive electrical circuitry representing an opacity transmitter which measures the light absorbence of a sample and outputs a direct current signal at a suitable current range, such as from 4 ma to 20 ma, which is inversely proportional to the percent transmission of the signal. The instrument functions as a conventional 4-20 ma transmitter with the current through the reference LED plus the current through the LED array source together with the current needed by the amplifier totals 4 ma at zero absorbence or 100% transmission and 20 ma at full scale. This relationship determines the value of individual currents for a given range of transmission for the two path lengths of the measure and reference light sources. A suitable reference LED and a photo cell are included in the circuitry. The two photo cells form a matched pair with the reference photo cell operating a differential amplifier and forming a reference signal which is indicative of a predetermined condition of oil mist opacity, this being indicated by absorption units or percentage transmission through the oil mist in the light detected by the reference cell. The LED light is at a wavelength which renders the oil transparent so that an oil coating on the light source and detector does not change the output. Light scatter from oil droplets in the sample cause attenuation of the signal.

BRIEF DESCRIPTION OF THE DRAWINGS

So that the manner in which the above-recited features, advantages and objects of the invention, as well as others which will become apparent, are attained and can be understood in detail, a more particular description of the invention, briefly summarized above, may be had by reference to the embodiments thereof illustrated in the appended drawings, which drawings form a part of this specification.

It is to be noted, however, that the appended drawings illustrate only typical embodiments of this invention and are not to be considered limiting of its scope, for the invention may admit to other equally effective embodiments.

DETAILED DESCRIPTION OF THE PREFERRED EMBODIMENT

Figure 1:
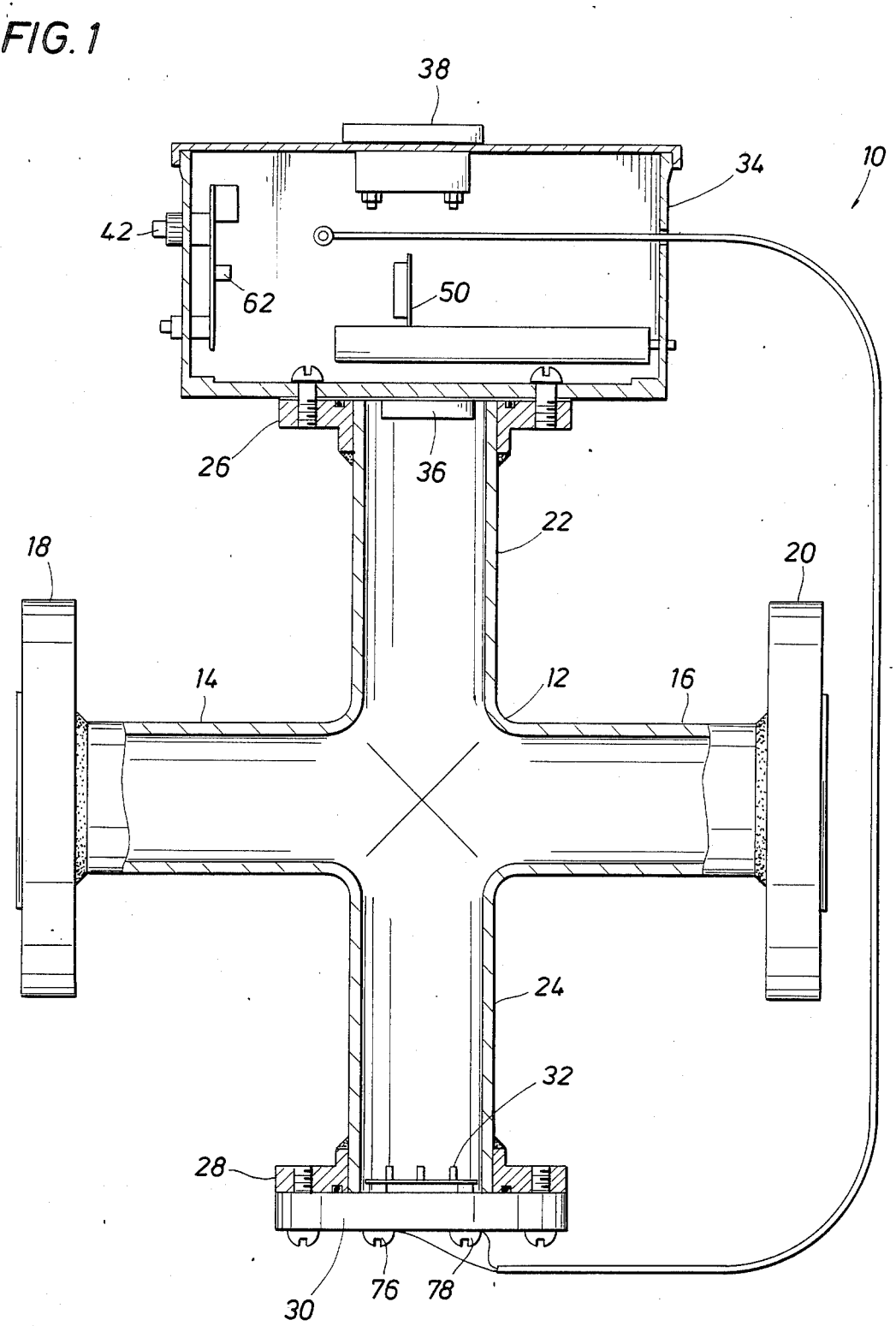
FIG. 1 is a sectional view through an oil mist monitor formed of a pipe cross having four legs, two legs being connected to conduct oil mist, and two legs mounting a suitable photo cell and LED display with associated circuitry for measuring opacity across the oil mist path.

Attention is first directed to FIG. 1 of the drawings where the numeral 10 identifies an oil mist monitor system. It is constructed in accordance with the teachings of this disclosure. More particularly in FIG. 1, a pipe cross will be described first and the various devices mounted on it will then be described. These devices will be related to the circuit components of FIG. 2 thereafter to complete a description of the apparatus shown in FIG. 1.

A pipe cross 12 includes legs 14 and 16. The legs 14 and 16 provide a straight through flow path. They are terminated at suitable flanges 18 and 20 deployed in accordance with industry standards to enable the pipe cross to be bolted in a piping system. In particular, it is intended for installation in a piping system between an oil mist generator and a device utilizing rotating equipment whereby the oil mist is required for operation of the equipment. It will be assumed that the oil mist is air borne through a stream of air flowing from left to right as shown in FIG. 1. The numeral 22 identifies a one cross arm and the opposite arm is identified at 24. The cross arms are preferably equal in length, arranged opposite to one another, and of suitable diameter which conveniently is the same diameter for the other two legs. Thus, the four legs are identical in diameter in the preferred embodiment and have approximately the same length. The length of the legs 22 and 24 can be varied, this normally being a scale factor in the construction of the device. It will be further observed that each of the two transverse legs terminates with suitable flanges, one flange being identified at 26 and the other flange at 28. They are used as mounting flanges and are transversely covered or closed.

An electrically insulative closure plate 30 is mounted on the flange 28 and suitable seals prevent leakage at that end of the equipment. The closure plate 30 is used as a mounting plate. Through the use of suitable stand off posts, several monochromatic light emitting devices are supported by the closure plate 30. They are identified by the numeral 32 and are preferably LED devices. One or more LEDs can be used. They are connected in series as will be described in detail in reference to FIG. 2. For the electrical output signal of the transmitter to be inversely linear with opacity, the light source output must be linear with the drive current. LED's provide monochromatic light output which is linear with current and therefore are quite effective in the disclosed circuitry.

Monochromatic light is emitted by the LEDs 32 and the light is transmitted to the facing measuring device. The flange 26 is fastened to an electrical box or housing 34 to support certain components on the box interior. The box 34 is composed of electrically insulative material. A seal is perfected at the juncture between the flange 26 and the box 34. This again prevents leakage through this part of the equipment. Moreover, the box wall supports a measure photo cell 36 cooperatively related in mist measuring relation with LED's 32. The photo cell 36 is preferably centered in the pipe just as the LEDs 32 are centered at the opposite side. This positioning locates the cooperative devices where they face one another so that light transmitted from the LEDs 32 passes through the oil mist flow path for detection at the photo cell 36. The photo cell is connected by suitable wiring (omitted for sake of clarity) which is connected to the circuitry inside the box 34. Conveniently, the box 34 has room on the interior to mount a meter movement 38 which is read from the exterior. The apparatus is completely closed and sealed and has no light windows. Oil droplets that would diffract light and, if on a window, would cause it to miss the detector, form on the detector but the light will not miss the detector because of its close proximity to the source.

Figure 2:
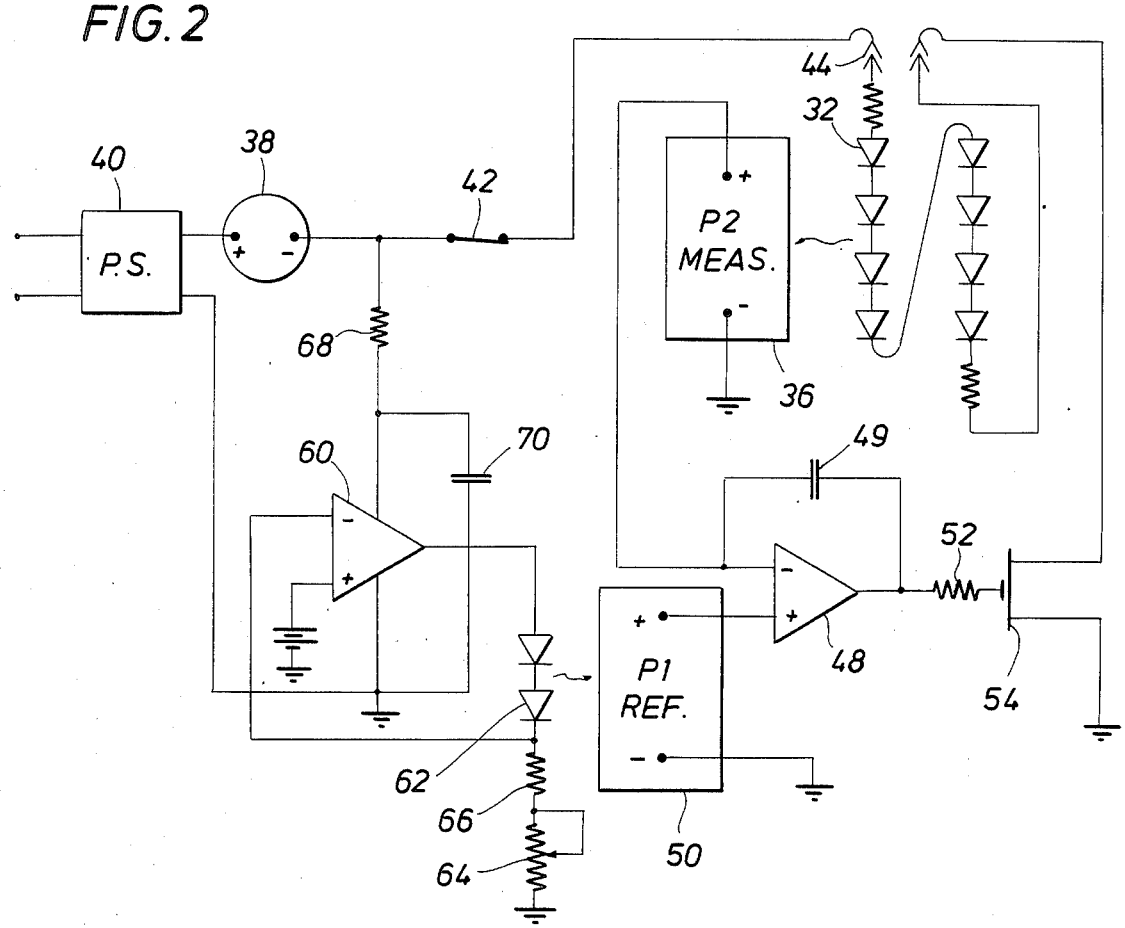
FIG. 2 is a schematic wiring diagram of the opacity measuring circuit installed in accordance with the structure of FIG. 1.

Attention is now directed to the schematic wiring diagram of FIG. 2. The numeral 40 identifies a current generating circuit which functions as a power supply. The power supply is preferably a 24 volt current limited power supply, which is preferably located in a closed, explosion proof environment perhaps remote from the oil mist monitor. The power supply has two output terminals with one connected to the meter 38. Recall that this is the meter movement shown in FIG. 1. This meter movement is connected through an interrupt switch 42 in series with the LEDs 32. For convenience sake, a suitable plug and jack is included at 44 to enable the LED display to be removed and conveniently replaced. The switch 42 provides an interruption that is used in a calibration procedure which will be described.

The numeral 48 identifies a differential amplifier. It is provided with two inputs and amplifies the difference in input voltages. One input is obtained from the photo cell 36. A second input is obtained from a reference photo cell 50. The two photo cells form input voltages which are subtracted from one another. The photo cell 50 is used as a reference (discussed in detail below) so that the variable signal from the photo cell 36 is contrasted with it. It is desirable to use two matched photo cells. Preferably, when one of the two is replaced, the other is replaced so that they age together. Photo cell aging is thus reduced to a minimum error, and the two signals thus provide an output differential signal which is indicative of the changes in measured light as will be described.

The amplifier 48 is output to a series resistor 52 which is connected to the gate of an FET transistor 54. That transistor regulates the current flow provided to the LEDs 32. That current flow passes through the LEDs and the switch 42. This current causes variations in the indication of the meter 38; that is, the meter 38 reflects changes indicative of variations in opacity arising from oil mist density and is therefore indicative of oil mist concentration. More will be noted concerning this in an example of operation. The speed response of the amplifier 48 is quite fast and therefore a capacitor 49 is provided as a dampener to prevent oscillation of the LED array and the power signal. A second differential amplifier is included at 60. The differential amplifier 60 maintains a constant current to reference LEDs 62. This current level is adjusted by means of an adjustable potentiometer 64 connected in series with a resistor 66. The resistors 64 and 66 in conjunction with the amplifier 60 fix and determine a reference current.

The LEDs 62 emit light for the reference photo cell 50. If this current is held steady, then the operation of the photo cells 36 and 50 provides a stable input to the differential amplifier 48 which nulls photo cell drift or aging. For instance, drift may occur with an increase in temperature. Drift may occur as a result of aging. Drift may occur for other reasons; all drift factors are reduced substantially to zero by the implementation of the photo cells 50 and 36 preferably positioned close to one another, installed simultaneously, aged equally, and replaced jointly. As will be understood, the current applied to the LEDs 62 is intended to be constant. For example, the current may be in the range of about 200 mv which is compared to the voltage across the potentiometer for constant current development for constant light value emission from the LED's. It is adjustable for calibration which will be described. Metal screws may secure the reference LED's to the electrically insulative box and also make electrical connection with the LED circuit. The screws, being exposed externally of the box, enable checking of the electrical integrity of the reference LED's without requiring opening of the box.

The constant current is thus obtained from the amplifier 60. While one terminal is tied to a reference voltage, the other is connected to the cathode of the diode string to assure that the current level is set and is steady for a given setting on the resistor 64. As will be understood, a series resistor 68 and a capacitor 70 are included. The resistor 68 defines the maximum current the circuit can draw in the event of a short in the circuit and thus is a safety factor. The capacitor 70 basically functions with the resistor 68 as a noise pick-up filter such as for 60 cycle noise. The circuitry forms a unique two wire transmitter circuit.

Operation should now be considered. To understand the operation, the components shown in FIG. 2 are positioned in the following manner. The LEDs 32 are located as shown in FIG. 1 opposite the photo cell 36. Preferably, the photo cells 36 and 50 are immediately adjacent to one another so that they experience the same environmental conditions. The reference LED 62 is physically positioned within the electrical box for direct illumination of the reference photo cell 50. All of this equipment is enclosed in the box 34 which is opaque; therefore, the only source of light within the box is the monochromatic light from the light emitting diodes 62 and that light impinges on the reference photo cell 50. The reference photo cell 50 is isolated optically from the variable photo cell 36, the two being located on opposite sides of the wall of the box 34.

Figure 3:
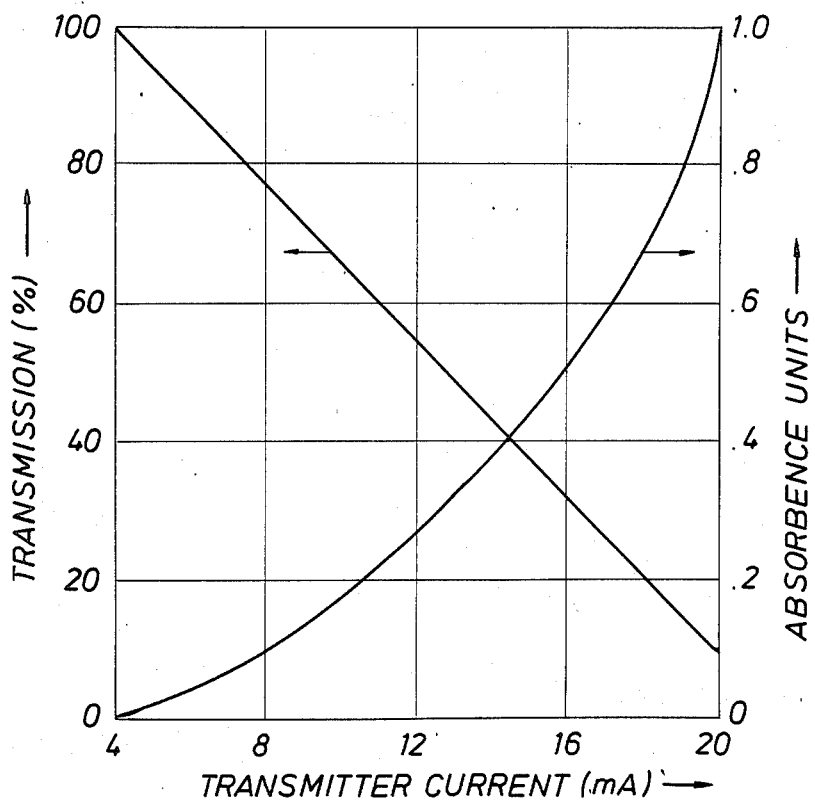
FIG. 3 is a graphical representation of percent transmission and absorbence units in relation to transmitter current, illustrating the inversely proportional relation of light absorbence and transmitter current.

Typically, the meter movement 38 in conjunction with the circuit components establishes a minimum current flow. The range of current flow is within the range permitted by the process instrument industry standard for transmitters and begins at about 4 ma and runs up to about 20 ma. For definitional purposes, one hundred percent transmission corresponds to 0.0 absorbence units while ten percent corresponds to 1.0 absorbence units as reflected graphically in FIG. 3. This then defines a calibration curve wherein the variable is indicated by current through the meter 38.

Consider the following as an example of scale factors encountered in a typical installation. Using a cross where the photo cell and LEDs are located about ten inches apart, and making an arbitrary requirement of sixty percent indicative of a suitable flow of oil mist, a calibration screen enabling sixty percent transmission is inserted through the pipe cross. Beer's law determines the absorbence, or the percent transmission may be the variable of interest. In other words, an absorbence of 0.73 corresponds to a reading of sixty percent of scale.

Figure 4:
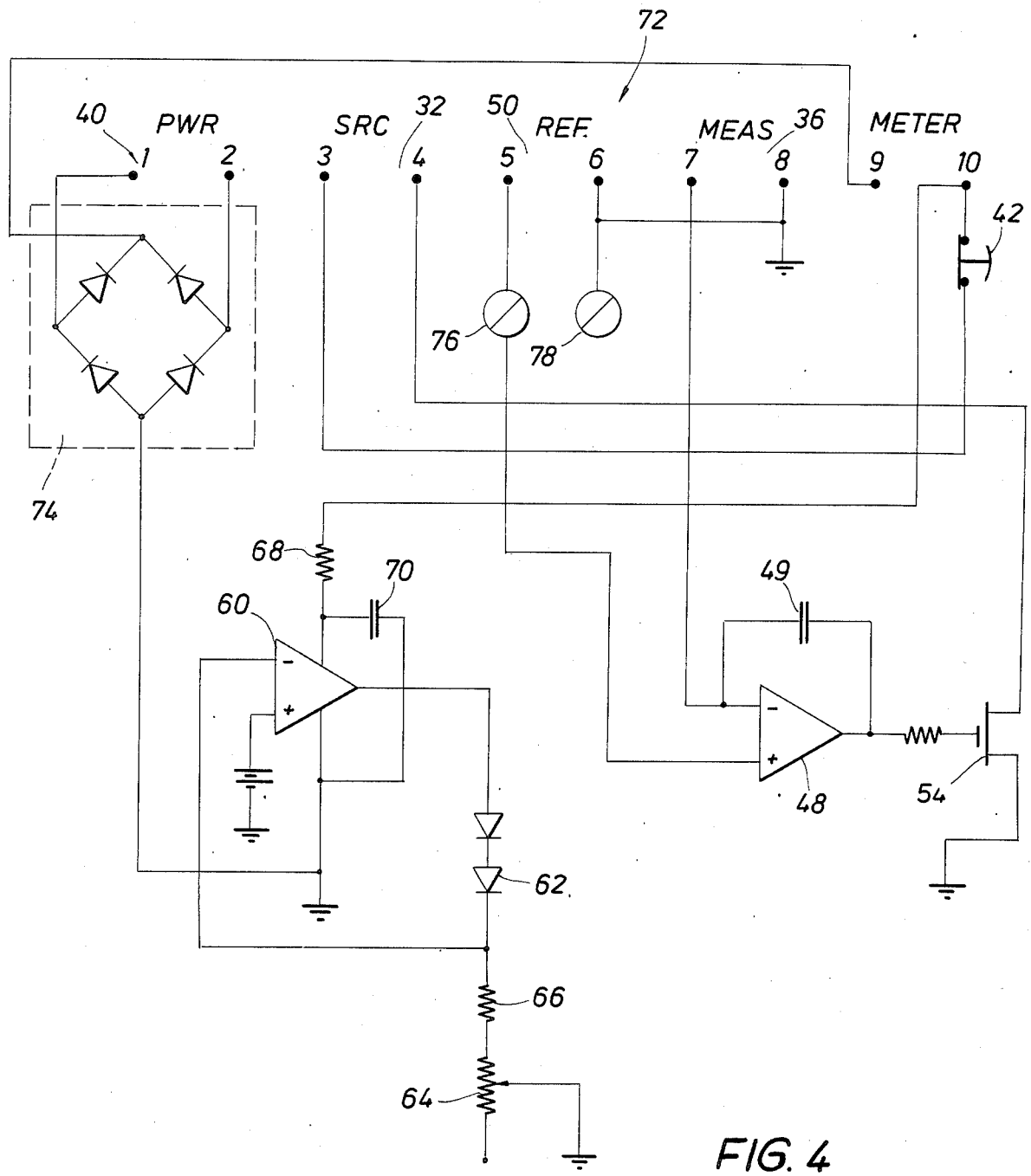
FIG. 4 is a schematic wiring diagram of the main circuit board of the opacity measuring circuit, including a major portion of the circuit of FIG. 2.

With reference now to FIG. 4, a circuit board electrical schematic wiring diagram is shown which basically discloses the various parts of the circuit illustrated in FIG. 2, with exception of the meter and LED array. Like parts bear like reference numerals for the sake of simplicity. The circuit board 72 is connected at 1 and 2 with a bridge rectifier circuit 74 which prevents the 4–20 ma power input from being improperly connected. The 24 volt current is the actual signal. The array of measure LEDs 32 is connected across circuit board connectors 3 and 4 while the reference photo cell 50 is connected across connectors 5 and 6. At connectors 7 and 8, the measure photo cell 36 is coupled with the circuit. Meter terminals 9 and 10 of the circuit board provide for connection of meter equipment into the circuit for local indication.

A pair of metal screws 76 and 78 secure the measure LED array to the closure plate 30. The closure plate is composed of non-metallic electrically insulative material such as plastic and the screws 76 and 78 make electrical contact with the circuit. Thus a test circuit may be positioned across the screws without removing the plate 30 and without otherwise opening the closed chamber to enable safe and efficient checking of the integrity of the internal LED array. In the event a LED is burned out such may be easily and quickly determined by external electrical inspection.

While the foregoing is directed to the preferred embodiment, the scope thereof is determined by the claims which follow.

What is claimed is:

1. For use with an oil mist genrating apparatus forming an oil mist conveyed along a conduit with an air flow to apparatus using such an oil mist, oil mist monitoring apparatus comprising:
   (a) a laterally extending open interior housing means adapted to be positioned at a location to conduct air borne oil mist thereacross;
   (b) first monochromatic light forming means in said housing means for forming light illuminating said housing means across the oil mist passing therethrough;
   (c) first light detector means in said housing means located to detect light from said monochromative light forming means across the oil mist passing through said housing means and forming a first output signal;
   (d) a cooperative joinder to said housing means including, first and second separate flange mounting means adapted to join to said housing means to position and locate said first monochromatic light forming means and said first light detector meansand for directing light across said housing means;
   (e) second light forming means providing reference light wherein said first light forming means and said second light forming means are similar to each other to form light in equal quantity in response to equal light forming currents;
   (f) second light detector means positioned to detect reference light from said second light forming means;
   (g) light opaque container means enclosing said second light forming means and said second light detector means to prevent internal light from entering therein and further positioning said second light detector means to view said second light forming means and forming a second output signal;
   (h) means mounting said first and second light forming means in sufficient proximity to each other for exposure to common temperature variations;
   (i) circuit means electrically comparing said first and second output signals to provide an output signal inversely related to opacity of the oil mist in said housing means; and
   (j) output means provided with said output signal to indicate oil mist opacity.

2. The apparatus of claim 1 wherein said first and second light forming means are similar monochromatic light forming means.

3. The apparatus of claim 2 wherein:
   (a) constant voltage means powers said second monochromatic light forming means to form monochromatic light at a reference level;
   (b) differential amplifier means connected to said second light detector means;
   (c) said differential amplifier means having a second input for said first light detector means;
   (d) said differential amplifier means forming a difference signal output to said output means; and
   (e) said output means having a current range with a minimum determined in part by current flow at minimum light on said first light detector means.

4. The apparatus of claim 3 wherein said output means comprises a meter movement; and said output means measures current flow to said first light detector means through a switch means having a normally conductive state.

5. The apparatus of claim 3 wherein said output means comprises a meter movement serially connected through plug and socket means to said first light detector means to enable replacement thereof.

6. The apparatus of claim 3 wherein said output means is a current meter having a range of 4 to 20 ma, and the current levels at ends of the range indicate minimum and maximum values of opacity.

7. The apparatus of claim 6 wherein minimum current flow is, in part, established by current flow to sustain operation of connected circuitry.

8. The apparatus of claim 2, wherein said electrical output signal is a direct current signal which is inversely proportional to the percent transmission of the light signal of said emitting means.

9. The apparatus of claim 2 including a power signal circuit wherein the current thereof is at a minimum when said oil mist flow path is clear and increases as the opacity of the oil mist sample in said oil mist flow path increases.

10. The apparatus of claim 2 wherein said light forming means comprise LEDs.

11. The apparatus of claim 2 including a common support means for said first and second light forming means.

12. The apparatus of claim 1 wherein said housing means comprises:

(a) a pipe cross having two opposing arms for receiving said first monochromatic light forming means and said first light detector means in opposing relationship;

(b) two additonal opposing arms adapted to be connected to a pipe conducting oil mist therealong; and (c) said arms terminating in flanges enabling connection to said housing means.

13. The apparatus of claim 12 wherein said arms are mutually perpendicular to one another, and
 wherein two of said arms are positioned horizontally to prevent oil mist from settling in one of said arms.

14. The apparatus of claim 1 wherein said output means comprisesa meter forming a visual indication of current flowing therethrough, and is connected to said circuit means to measure the output signal current therefrom.

15. The apparatus of claim 1 wherein said light opaque container means comprises a closed opaque housing having a portion thereof formed of a non-conductive material, and further including a pair of test probe means extending through and into the interior of said container means, said probes contacting an internally located circuit within said container means for providing electrical power for operation of said second light forming means and are exposed on the exterior permitting access for testing without penetration of the interior of said container means.

* * * * *

UNITED STATES PATENT AND TRADEMARK OFFICE
CERTIFICATE OF CORRECTION

PATENT NO. : 4,687,327

DATED : August 18, 1987

INVENTOR(S) : Michael R. Wheeless

It is certified that error appears in the above-identified patent and that said Letters Patent is hereby corrected as shown below:

Column 6, line 17, "monochromative" should read --monochromatic--.
Column 6, lines 25, 26, "mean-sand" should read --means and--.
Column 8, line 15, "comprisesa" should read --comprises a--.

Signed and Sealed this

Nineteenth Day of April, 1988

Attest:

DONALD J. QUIGG

*Attesting Officer*   *Commissioner of Patents and Trademarks*